United States Patent
Yao et al.

(10) Patent No.: US 9,078,753 B2
(45) Date of Patent: Jul. 14, 2015

(54) SURGICAL ORTHOPEDIC IMPLANTS MADE FROM WEAR-RESISTANT COBALT—CHROMIUM—MOLYBDENUM ALLOYS

(75) Inventors: Matthew Yao, Belleville (CA); Rachel Collier, Belleville (CA); Danie DeWet, Kingston (CA)

(73) Assignee: KENNAMETAL INC., Latrobe, PA (US)

( * ) Notice: Subject to any disclaimer, the term of this patent is extended or adjusted under 35 U.S.C. 154(b) by 224 days.

(21) Appl. No.: 13/463,313

(22) Filed: May 3, 2012

(65) Prior Publication Data

US 2013/0297037 A1 Nov. 7, 2013

(51) Int. Cl.
| | |
|---|---|
| A61K 6/04 | (2006.01) |
| A61F 2/30 | (2006.01) |
| A61L 27/04 | (2006.01) |
| A61L 27/50 | (2006.01) |
| C22C 1/04 | (2006.01) |
| C22C 30/00 | (2006.01) |
| C22C 19/07 | (2006.01) |

(52) U.S. Cl.
CPC .............. *A61F 2/30* (2013.01); *A61F 2/3094* (2013.01); *A61L 27/045* (2013.01); *A61L 27/047* (2013.01); *A61L 27/50* (2013.01); *C22C 1/0433* (2013.01); *C22C 19/07* (2013.01); *C22C 30/00* (2013.01)

(58) Field of Classification Search
CPC .................................. A61K 6/04; C22C 19/07
USPC ................ 72/352; 164/47; 419/1; 623/23.53
See application file for complete search history.

(56) References Cited

U.S. PATENT DOCUMENTS

| | | |
|---|---|---|
| 4,116,724 A | 9/1978 | Hirschfeld et al. |
| 7,520,947 B2 | 4/2009 | Kennedy et al. |
| 7,771,775 B2 | 8/2010 | Lawrynowicz et al. |

(Continued)

FOREIGN PATENT DOCUMENTS

| | | |
|---|---|---|
| EP | 0509910 | 10/1992 |
| EP | 804934 A2 | 11/1997 |
| FR | 2750867 | 1/1998 |

(Continued)

OTHER PUBLICATIONS

Abstract of JP61003859; Jan. 9, 1986.

(Continued)

*Primary Examiner* — Kaj K Olsen
*Assistant Examiner* — Alexander Polyansky
(74) *Attorney, Agent, or Firm* — Larry R. Meenan

(57) ABSTRACT

A surgical implant component comprising an implant component body manufactured from an alloy comprising from about 23 to about 33 wt % Cr, from about 8 to about 20 wt % Mo, from about 0.05 to about 1.5 wt % Si, from about 0.35 to about 3.5 wt % C, from about 40 to about 60 wt % Co, and incidental impurities. The implant component alloy has an atomic % ratio of (Cr+Mo+Nb)/Co of at least 0.59, a matrix metallurgical microstructure comprising between about 45% and about 85% by volume face-centered cubic structure, and between about 15% and about 55% by volume hexagonal close-packed structure; and a Rockwell C hardness of greater than 35. A method for manufacturing a surgical implant component body for a surgical implant by a manufacturing method selected from the group consisting of casting, forging, and powder metallurgy pressing-plus-sintering from an alloy.

22 Claims, 12 Drawing Sheets

(56) References Cited

U.S. PATENT DOCUMENTS

| | | | |
|---|---|---|---|
| 7,867,281 B2 | 1/2011 | Carroll | |
| 2004/0109785 A1 | 6/2004 | Lindigkeit | |

FOREIGN PATENT DOCUMENTS

| | | |
|---|---|---|
| JP | 61003859 | 1/1986 |
| JP | 61026739 | 2/1986 |
| JP | 62136544 | 6/1987 |
| JP | 62164844 | 7/1987 |
| JP | 10204564 | 8/1998 |
| JP | 2007111712 | 5/2007 |
| WO | 2005007909 A2 | 1/2005 |

OTHER PUBLICATIONS

Abstract of JP61026739; Feb. 6, 1986.
Abstract of JP62136544; Jun. 19, 1987.
Abstract of JP62164844; Jul. 21, 1987.
Search Report, Great Britain Application No. 1307837.3, dated Nov. 21, 2013, 2 pages.
Okazaki, Yoshimitsu et al., "Corrosion resistance and corrosion fatigue strength of new titanium alloys for medical implants without V and Al", Materials Science and Engineering, A213, 1996, pp. 138-147.
Pypen, C.M.J.M et al., "Comparison of the cytotoxicity of molybdenum as powder and as alloying element in a niobium—molybdenum alloy", Journal of Materials Science: Materials in Medicine 9, 1998, pp. 761-765.
Niinomi, Mitsuo et al., "Recent Metallic Materials for Biomedical Applications", Metallurgical and Materials Transactions A, 2002, vol. 33, No. 3, pp. 477-486.
Puleo, David et al., "Acute toxicity of metal ions in cultures of osteogenic cells derived from bone marrow stromal cells", Journal of Applied Biomaterials, 1995 Summer, vol. 6, Issue 2, pp. 109-116.
Clark, G.C.F.et al., "The effects of proteins on metallic corrosion", Journal of Biomedical Materials Research, 1982, vol. 16, pp. 125-134.
Jan. 9, 2014—Office_Action.

SURGICAL ORTHOPEDIC IMPLANTS MADE FROM WEAR-RESISTANT COBALT—CHROMIUM—MOLYBDENUM ALLOYS

FIELD OF THE INVENTION

This invention is directed to surgical orthopedic implants where enhanced wear resistance is required.

BACKGROUND OF THE INVENTION

A cobalt-chromium-molybdenum (Co—Cr—Mo) metallic alloy specified by ASTM F75 is commonly used for surgical implants such as for prosthetic knees, hips, shoulders, elbows, wrists, ankles, fingers, toes and spinal elements because of the alloy's strength, corrosion resistance, and biocompatibility. This Co—Cr—Mo alloy has greater wear resistance than stainless steels and titanium alloys. The nominal composition of the F75 alloy is 27.00 to 30.00% Cr, 5.00 to 7.00% Mo, 0.35% C maximum, 1.0% Si maximum, 0.50% Ni maximum, with balance of Co and other inevitable trace elements and impurities. All percentages herein are by weight, unless indicated otherwise.

The most commonly used materials in the friction pair of endoprostheses include metal-on-UHMWPE (ultra-high molecular weight polyethylene) (about 85%), ceramics-on-UHMWPE (7.2%), metal-on-metal (5.3%), and ceramics-on ceramics (2.5%). Many factors influence wear rates of materials pairs. These factors include the types of materials, contact stresses, surface hardness, surface roughness, type of articulation due to motion, number of cycles, solution particle count and distribution, oxidation of materials, and surface abrasions of both metal and polyethylene particulates.

As the articulating surfaces of orthopedic implants wear and corrode, products including plastic wear debris, metallic wear particles, and metallic ions will be released into the body, transported to and absorbed by bone, blood, the lymphatic tissue, and other organ systems. The polyethylene wear particles have been shown to produce long term bone loss and loosening of the implant. And, even very low concentrations of metallic wear particles and metallic ions are suspect in causing adverse toxic, inflammatory, and immunologic tissue reactions.

Although the ASTM F75 Co—Cr—Mo alloy is relatively well tolerated in the body, biological complications could occur which sometimes are due to the insufficient wear resistance of the alloy and the presence of the nano-size metal particles from wear debris of the metal-on-metal or metal-on-UHMWPE articulating joints. While ASTM F75 alloy is biocompatible in bulk form, it causes severe inflammatory reactions when nano-size particles are absorbed by tissue cells, potentially causing metallosis and tissue death. The only solution to the metal-on-metal problem is to reduce amount of wear debris. Hence there is a need for a non-toxic, non-allergenic, and biocompatible Co—Cr—Mo alloy with improved wear resistance over ASTM F75.

Metal allergy is an adverse reaction to the metallic ions which are released from an alloy by the action of sweat and other body fluids. In dentistry, Co, Cr, and Ni have been associated with metal allergy, and the use of Ni is rapidly being abandoned. M. Niinomi: Function Mater., 2000, vol. 20, pp. 36-44, reports metal allergy rates for Hg, Ni, Co, Sn, Pd, Cr, Cu, Pt, Zn, Au, Cd, and Sb.

The effects of metal ions released from orthopedic implants on nearby bone cells remain largely unknown. The problem is primarily the death of muscle tissue from the effects of metal ions, leading to bone loss. David A. Puleo, Winston W. Huh, *Acute toxicity of metal ions in cultures of osteogenic cells derived from bone marrow stromal cells*, Journal of Applied Biomaterials, Volume 6, Issue 2, pages 109-116, Summer 1995, revealed that $Cr^{6+}$ was grossly cytotoxic; $Co^{2+}$, $Mo^{6+}$, $Fe^{3+}$, and $Ni^{2+}$ were moderately cytotoxic; and $Ti^{4+}$, $Al^{3+}$, $V^{5+}$, and $Mn^{2+}$ were minimally toxic. Ion solutions representing Co—Cr—Mo and 316 L stainless steel were moderately toxic; solutions representing Ti-6Al-4V were toxic at only the highest concentrations used. These results show that metal ions associated with Co—Cr—Mo and 316 L stainless steel are toxic to osteogenic cells at concentrations approximating those measured in the fibrous membrane encapsulating orthopedic implants.

In another study (G. C. F. Clark and D. F. Williams, *The effects of proteins on metallic corrosion*, Journal of Biomedical Materials Research, Vol. 16, 125-134 (1982)), the corrosion of the pure metals Al, Co, Cu, Cr, Mo, Ni, and Ti and of a Co—Cr—Mo casting alloy in buffered saline with and without the presence of the proteins serum albumin and fibrinogen was investigated. The corrosion of Al and Ti was unaffected by the protein. The corrosion rates of Cr and Ni showed a slight increase, while Co and Cu dissolved to a very much greater extent in the presence of the protein. The Mo demonstrated resistance to corrosion by the protein.

Pypen et al., *Comparison of the cytotoxicity of molybdenum as powder and as alloying element in a niobium-molybdenum alloy*, Journal of Materials Science: Materials in Medicine 9 (1998) 761-765), reported the cytotoxicity of the close-packed Nb metal and the Nb—Mo alloys based on a 72-hour direct contact test. Compared to a negative control (UHMWPE), Mo was moderately toxic; and Nb and Nb—Mo alloys were non-toxic.

Kennedy et al. U.S. Pat. No. 7,520,947 discloses work-hardening the low-carbon F75 type medical implant alloy by cold working such as by drawing followed by aging, or otherwise to impart wear resistance. For wrought shapes, a disadvantage of this is that substantial machining of the work-hardened wrought shape is required to yield the final product shape; which is especially difficult and expensive in view of the work hardening. For components produced by powder metallurgy or casting, the intricacy of the shape substantially complicates and in many instances renders impractical most work hardening.

SUMMARY OF THE INVENTION

Briefly, therefore, the invention is directed to a surgical implant component of a knee, hip, shoulder, elbow, wrist, ankle, finger, toe or spine, the implant component comprising an implant component body manufactured from an alloy comprising from about 23 to about 33 wt % Cr, from about 8 to about 20 wt % Mo, from about 0.05 to about 1.5 wt % Si, from about 0.35 to about 3.5 wt % C, and from about 40 to about 60 wt % Co; wherein the alloy has an atomic % ratio of (Cr+Mo+Nb)/Co of at least 0.59; and wherein the implant body has a metallurgical microstructure comprising between about 45% and about 85% by volume face-centered cubic structure, and between about 15% and about 55% by volume hexagonal close-packed structure.

The invention in another aspect is a method for manufacturing a surgical implant component body for a surgical implant comprising forming the surgical implant component body by a manufacturing method selected from the group consisting of casting, forging, and powder metallurgy pressing-plus-sintering from an alloy comprising from about 23 to about 33 wt % Cr, from about 8 to about 20 wt % Mo, from about 0.05 to about 1.5 wt % Si, from about 0.35 to about 3.5 wt % C, and from about 40 to about 60 wt % Co; wherein the alloy has an atomic % ratio of (Cr+Mo+Nb)/Co of at least 0.59; and excluding any cold working by rolling, drawing, swaging, shot-peening or laser-peening.

DETAILED DESCRIPTION OF PREFERRED EMBODIMENTS

Figure 1:
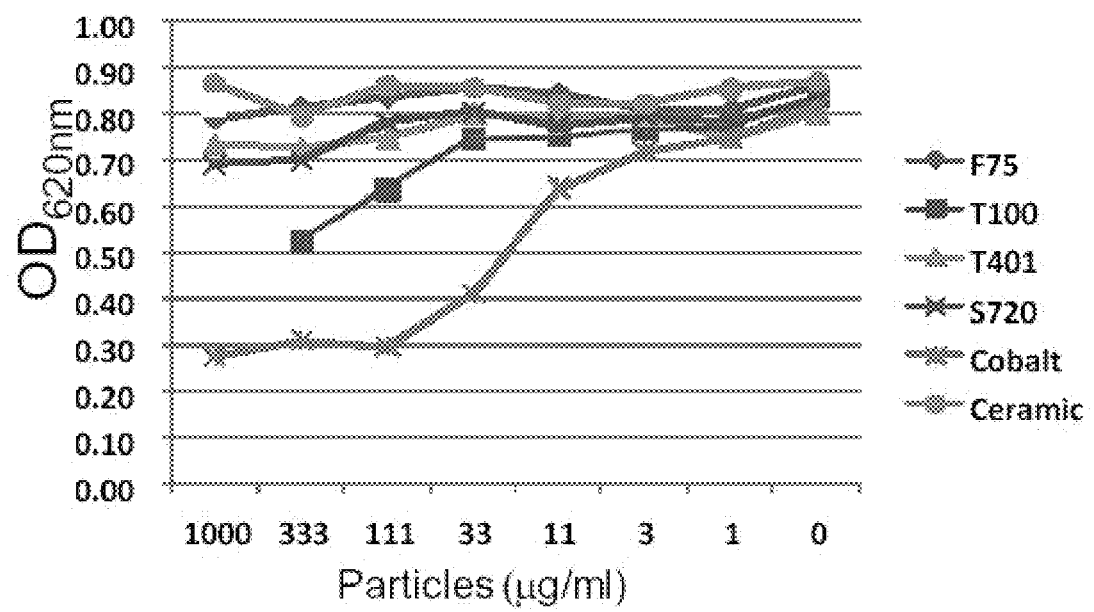
FIGS. 1 and 2 are graphical illustrations demonstrating cytotoxicity levels.

The present invention is a Co—Cr—Mo component of an orthopedic implant with biocompatibility and improved wear resistance to reduce the release of metal ions into the host. The orthopedic implant is for any one of knees, hips, shoulders, elbows, wrists, ankles, fingers, toes or spinal elements.

The invention is based on a discovery that alloys having higher Cr, higher Mo, and lower Co are necessary to manufacture non-toxic, non-allergenic and biocompatible implants with improved wear resistance as compared to current implants manufactured from the ASTM F75 alloy. In particular, it has been discovered that having a higher ratio of Cr+Mo+Nb to Co in combination with greater C content in comparison to the current implant alloy substantially yields surprisingly different crystal structure characteristics. It also improves hardness and wear resistance, which are critical to the efficacy of the implant and its long-term safety in the environment including wear and dissolution fluids within the host. The implants of the invention therefore are made from a Co—Cr—Mo alloy having a (Cr+Mo+Nb)/Co ratio in atomic percent of at least 0.59.

Chromium improves wear resistance due to work hardening and the formation of chromium carbides. Chromium forms a stable chromium oxide protective film on the alloy surface in an atmosphere at high temperatures, the protective film contributing to corrosion and oxidation resistance. For Cr to produce this effect in the present formulation, it is necessary that the amount of Cr should be at least 17 wt %. However, an excess amount more than 35 wt % is not desirable because it causes a harmful phase to precipitate out, making the alloy brittle. To safely avoid these ill effects, the invention is formulated to have a Cr content in the range of about 23 to about 33 wt %. This express Cr content requirement is independent of the requirement described above as to the ratio of (Cr+Mo)/Co. In other words, an implant that meets the >0.59 ratio requirement but does not have at least about 23 wt % Cr is not within the scope of the invention.

Molybdenum promotes work hardening, improve wear resistance, and increased high-temperature strength through solid solution strengthening. Molybdenum may be used in the invention alone for this purpose, preferably. Alternatively, Mo may be supplemented with Nb, W, and/or Ta for solid solution strengthening. The wear resistance of these cobalt-based alloys is somehow related to the low stacking fault energy of these austenitic materials. Molybdenum alone will not produce the desired effect if added in an amount of 5 wt % or less, or will form a harmful phase if added in an amount more than 20 wt %. The present invention therefore employs Mo in a range of from about 8 wt % to about 20 wt %, preferably from 10 to 20 wt %. This express Mo content requirement is independent of the requirement described above as to the ratio of (Cr+Mo)/Co. In other words, an implant that meets the >0.59 ratio requirement but does not have at least about 8 wt % Mo is not within the scope of the invention.

One alternative embodiment of the invention incorporates the optional element Nb. Niobium is less soluble than Mo in the cobalt matrix. Also, Nb will form a harmful phase added in an amount more than 5 wt %. Where Nb is used, therefore, it is incorporated in a concentration of up to 2.5 wt %, preferably between 1.8 and 2.2 wt % in certain embodiments.

Manganese increases stacking-fault energy (SFE) in the alloys of the invention, and acts as a deoxidizer during melting and casting of the alloy, thereby improving manufacturability. Manganese of 0.02 wt % or less does not produce the desired effect, and manganese more than 1.5 wt % negatively impacts the ductility of the resulting material. Manganese is therefore included in these alloys in a range of between about 0.05 and about 1.5 wt %, preferably in a range of between about 0.2 and 1 wt %.

Silicon reduces stacking-fault energy (SFE) in the alloys of the invention, contributes to work hardening, and lowers the melting point of the resulting material, thereby improving manufacturability. Silicon of 0.02 wt % or less does not produce the desired effect, and silicon more than 1.5 wt % negatively impacts the ductility of the resulting material. Silicon is therefore included in these alloys in a range of between about 0.05 and about 1.5 wt %, preferably in a range of between about 0.2 and 1 wt %.

A substantial distinction in comparison to the prior F75 implant alloy is the requirement for a greater C concentration. While the maximum C permitted in F75 has been 0.35 wt %, the present invention requires more than 0.35 wt %, and in preferred embodiments between 1.5 and 3.5 wt %. This higher C content in combination with higher Mo content (and optional Nb) together with the Cr enhances solid solution strengthening and yields greater carbide formation which enhances hardness and wear resistance. In fact, the effect of C as a solid solution strengthener is 100 times that of Ni.

The implant components of the invention also require that the Co concentration be held strictly to below 60 wt %, i.e., between 40 and 60 wt %. A Co concentration above 60 wt % is avoided because pure cobalt has been shown to be cytotoxic.

The alloy from which the implant components are formed may also contain small amounts of other inevitable trace elements and impurities, with the total concentration of such being less than about 4 wt %, preferably less than about 2 wt %.

The implant components of the invention are formed by casting, powder metallurgy, forging or other manufacturing processes understood in the art to be suitable for cobalt-based alloys.

Examples of alloys used to formulate the implants of the invention (703, 701, 704, 720, 790, and 712; and 22 and 28) in chemical comparison to the currently used implant alloy F75, to T401, to T100, to pure Co, and to ceramic are as follows:

| Material | Co | Cr | Mo | C | Fe | Ni | Si | Mn | Nb |
|---|---|---|---|---|---|---|---|---|---|
| 703 | 53.2 | 30.5 | 12 | 2.30 | 0.5 | 0.5 | 0.5 | 0.5 | |
| 701 | 51 | 31.5 | 13 | 2.50 | 0.5 | 0.5 | 0.5 | 0.5 | |
| 704 | 53.05 | 30 | 14 | 0.95 | 0.5 | 0.5 | 0.5 | 0.5 | |
| 720 | 45.05 | 32.5 | 18 | 2.45 | 0.5 | 0.5 | 0.5 | 0.5 | |

-continued

| Material | Co | Cr | Mo | C | Fe | Ni | Si | Mn | Nb |
|---|---|---|---|---|---|---|---|---|---|
| 790 | 54.8 | 26 | 14 | 3.20 | 0.5 | 0.5 | 0.5 | 0.5 | |
| 712 | 58.65 | 28.5 | 9 | 1.85 | 0.5 | 0.5 | 0.5 | 0.5 | |
| 22 | 58.7 | 24 | 12 | 0.50 | 0.5 | 3.3 | 0.5 | 0.5 | |
| 28 | 56.15 | 24 | 12 | 0.35 | 0.5 | 4.0 | 0.5 | 0.5 | 2 |
| F75 | 63.75 | 28 | 6 | 0.25 | 0.5 | 0.5 | 0.5 | 0.5 | |
| T401 | 58.05 | 17 | 22 | 0.20 | 0.5 | 0.5 | 1.25 | 0.5 | |
| T100 | 58.7 | | 32.5 | 0.08 | | | 8.8 | | |
| Cobalt Ceramic | 100 | | | | | | | | |

Comparison of (Cr+Mo+Nb)/Co atomic % ratio and hardness are as follows:

| Material | (Cr + Mo + Nb)/Co Atomic % ratio | Hardness HRC |
|---|---|---|
| 703 | 0.79 | 54 |
| 701 | 0.86 | 51 |
| 704 | 0.80 | 47 |
| 720 | 1.06 | 56 |
| 790 | 0.69 | 60 |
| 712 | 0.65 | 48 |
| 22 | 0.59 | 38 |
| 28 | 0.64 | 38 |
| F75 | 0.56 | 33 |
| T401 | 0.56 | 48 |
| T100 | 0.34 | 61 |
| Cobalt Ceramic | 0 | |

It is therefore shown that the implant components of the invention have a hardness of greater than 35 and up to 60 HRC, with certain embodiments having a hardness of greater than 45 or even greater than 50 and up to 60 HRC.

In implant component alloys in one embodiment have very strictly controlled impurities in that the Ni concentration is strictly controlled to no more than 1 wt %, preferably no more than 0.7 wt %. The Fe content is, similarly, strictly controlled to no more than 1 wt %, preferably no more than 0.7 wt %. These embodiments are manifest in the implant alloys of the 700 series presented above. In one preferred embodiment, the Ni content is even more strictly controlled to less than 0.1 wt.

The alloys 22 and 28 differ from the inventive alloys of the 700 series in that the 22 and 28 alloys contain much lower C (between 0.2 and 0.8 wt %), contain much higher Ni in the range of between 3 and 4.5 wt % and in the case of alloy 28, contain Nb. The substantially higher Ni content renders the 22 and 28 alloys inappropriate in certain instances.

The implant component alloy employed in the invention generally "comprises" the foregoing components in that its advantages are germane to the positively recited requirements of the Co, Cr, Mo, Si and Mo content, in combination with the required ratio of (Cr+Mo)/Co and microstructural requirements.

A significant aspect of the implants of the invention is that their matrix microstructure (aside and apart from carbides) is mixed face-centered cubic (FCC) and hexagonal close-packed (HCP); and is between about 45% and about 85% by volume FCC and between about 15% and about 55% by volume HCP. In one exemplary embodiment, the alloy contains between 75 and 85 vol % FCC and between 15 and 25 vol % HCP. In another exemplary embodiment, the alloy contains between 45 and 55 vol % of each of FCC and HCP. The advantage of this mixed structure is that ductility is maintained by the greater than about 45% FCC, while wear resistance is imparted by the more than about 15% HCP. The overall microstructure contains on the order of between about 10 and 35 wt % carbides. For example, certain embodiments have between 12 and 30 wt % carbides.

The implant component alloy employed in the invention generally "comprises" the foregoing components in that its advantages are germane to the positively recited requirements of the Co, Cr, Mo, Si and Mo content, in combination with the required ratio of (Cr+Mo)/Co and microstructural requirements. There are certain embodiments within this general scope wherein the alloy "consists essentially of" the positively recited alloying elements and excludes any other components which materially affect the basic and novel properties, which properties here are the Rockwell hardness and the required mixed FCC/HCP matrix microstructure containing 10 to 35 wt % carbides; and in any event excludes any other components in a concentration above 5 wt %. In other embodiments the alloy "consists of" these compositional requirements in that other non-recited components are strictly excluded.

The implant component of the invention has the substantial advantage that it is manufactured by straightforward forging, casting, powder metallurgy pressing-plus-sintering, or other methods without any significant work hardening other than the passive work hardening occurring during cooling. That is, there is no active work hardening. For example, there is no cold working by rolling, drawing, swaging, shot peening, and/or laser peening. The term "active work hardening" as used herein excludes the passive work hardening that occurs as the alloy is cooled from its formation temperature (the implant component formation temperature) to room temperature. The term "active work hardening" refers to methods of work hardening employing operations other than cooling, such as cold-working processes including rolling, drawing, swaging, shot peening, and laser peening. "Active work hardening" also encompasses aging processes which are component or companion operations of many cold-working methods. An advantage of this invention is therefore that in a preferred embodiment, the only work hardening imparted to the component is passive work hardening, and that the component is cold-working-free, and preferably active-work-hardening-free.

Example I

The biocompatibility and cytotoxicity of the implants of the invention was tested by examining particle-induced inflammation using an in vitro model with macrophage cell lines according to ISO 10993. Cobalt and ceramic nano particles were used as reference points. The viability of the cells in response to the metallic particles was measured as absorbance at wavelength 620 nm. The results are presented in FIG. 1. Alloy T100 and pure Co exhibited strong evidence of cytotoxicity. Alloys 720 and T401 showed no cytotoxicity and behaved similar to alloy ASTM F75 and to the ceramic (inert) samples.

Example II

Figure 2:
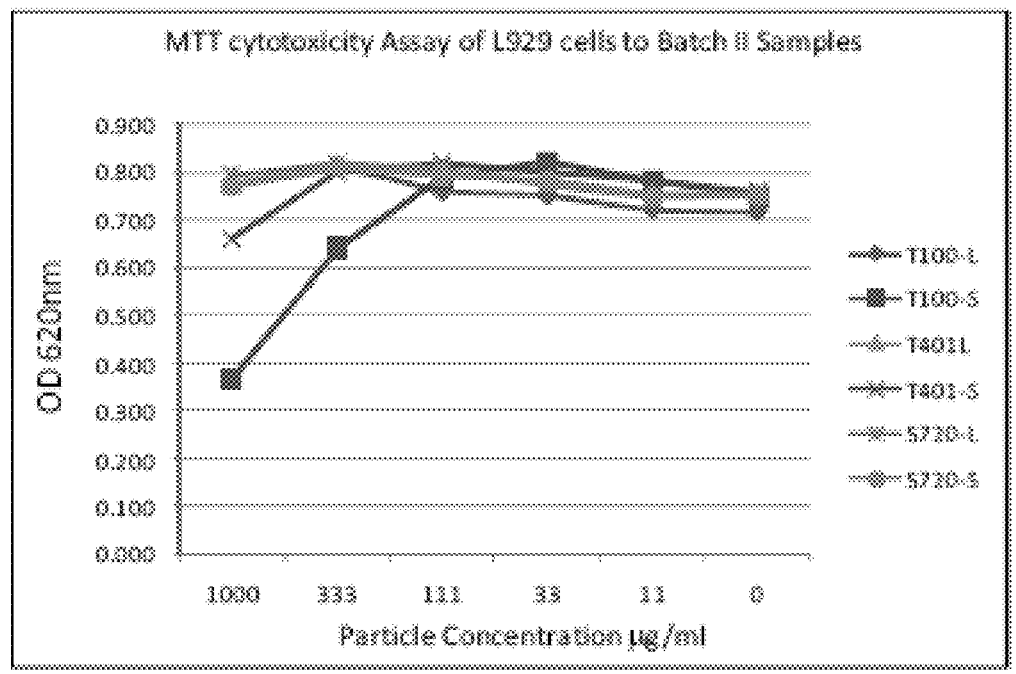

Coarse and fine metal particles of the 720 alloy were tested for cytotoxicity and compared to coarse and fine particles of T100 and T401. The results are presented in FIG. 2. The designation "L" is for larger particles which are essentially shards, while "S" designates smaller particles which are essentially dust.

Example III

Figure 3:
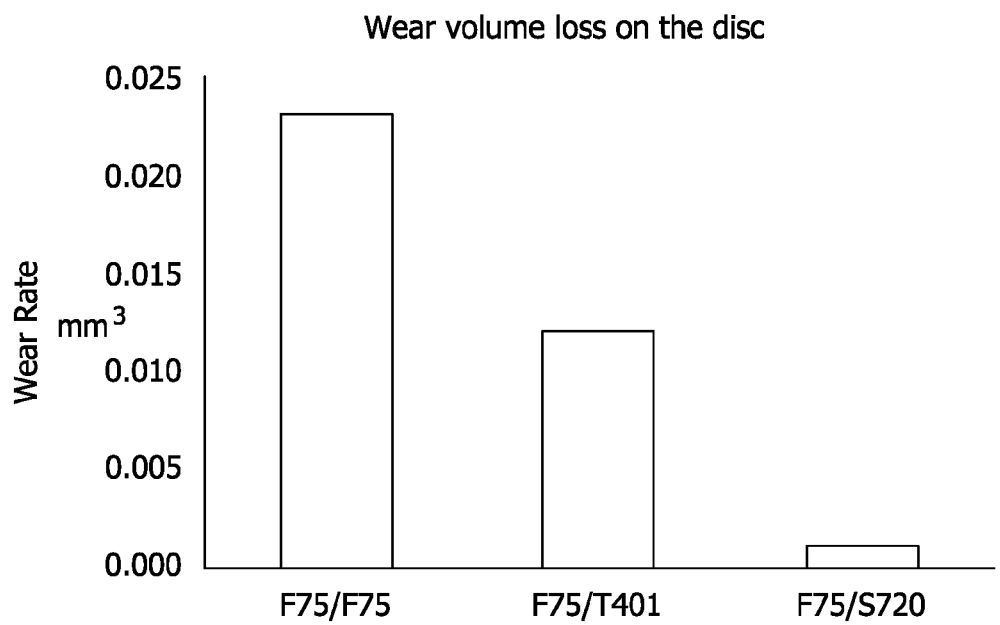
FIGS. 3 through 6 are graphical illustrations of comparative wear resistance.
Figure 4:
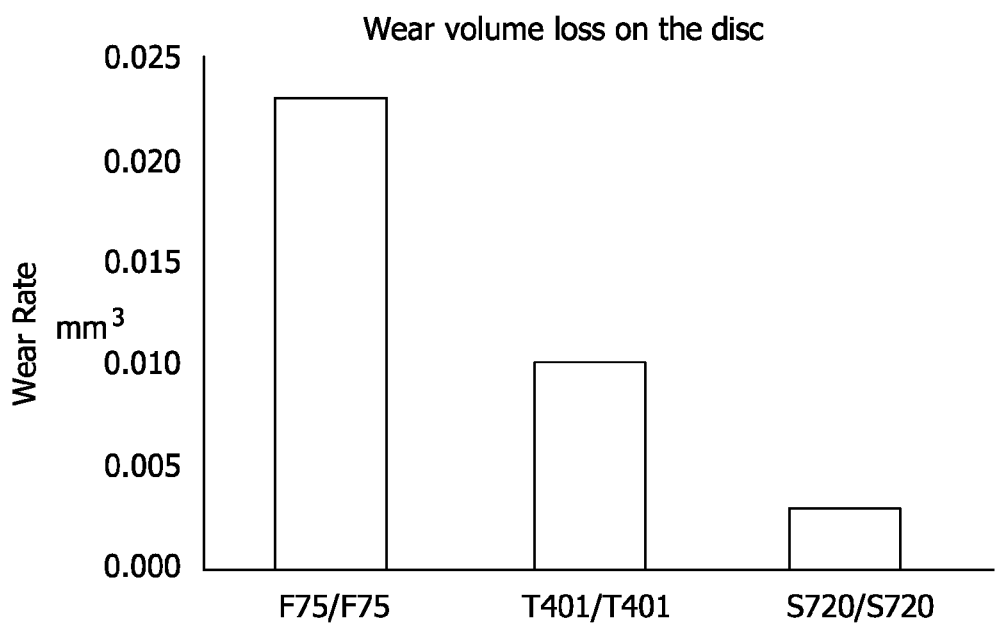

Metal-on-metal wear resistance tests were conducted using ASTM F75 pins against discs made of ASTM F75, T401 and 720 according to the ASTM G99 pin-on-disc wear test standard. The results are shown in FIG. 3. ASTM F75 showed ten times more wear than 720 disc. Also, self-mated metal-on-metal tests were conducted for ASTM F75, T401, and 720. The results are shown in FIG. 4. ASTM F75 couple showed eight times more wear than the Stellite 720 couple.

Example IV

Figure 5:
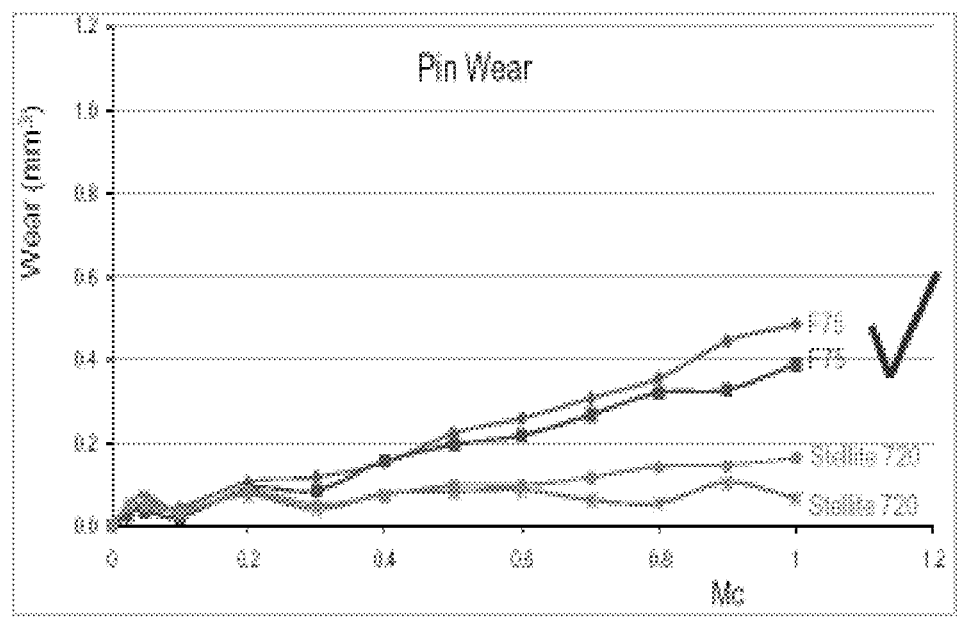
Figure 6:
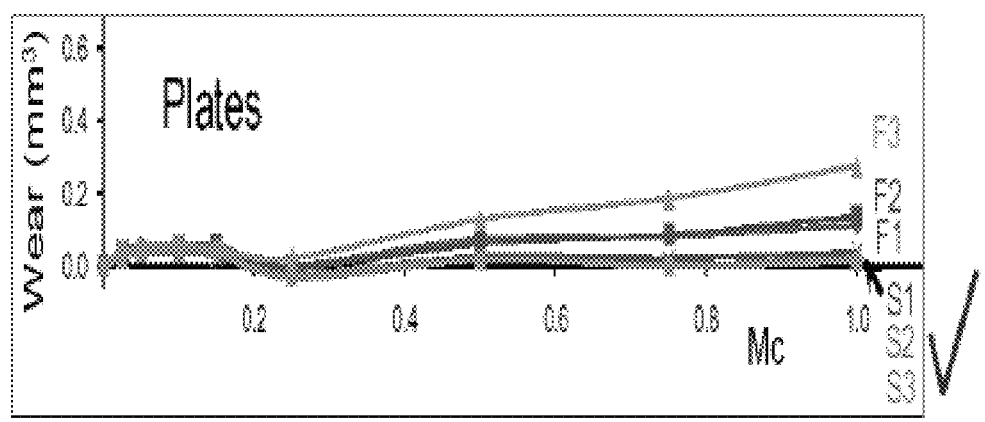

A pin-on-plate test was conducted in a chamber with alpha calf serum solution (protein 12 g/l) with both reciprocating and crossing path motion. Two wear testing rigs were used with different loads and contact stress. The test on custom apparatus was under a dead load of 9.81N and at about 28° C. The results are shown in FIG. 5. The two lines for F75 and 720 represent repeated tests. The units on the x axis are millions of cycles. The test on an OrthoPod rig was under pneumatic load of 80N and at about 37° C. The results are shown in FIG. 6, which shows three repeated tests for F75 (lines F1, F2, and F3), and three repeated tests for 720 (S1, S2, and S3).

Example V

Figure 7:
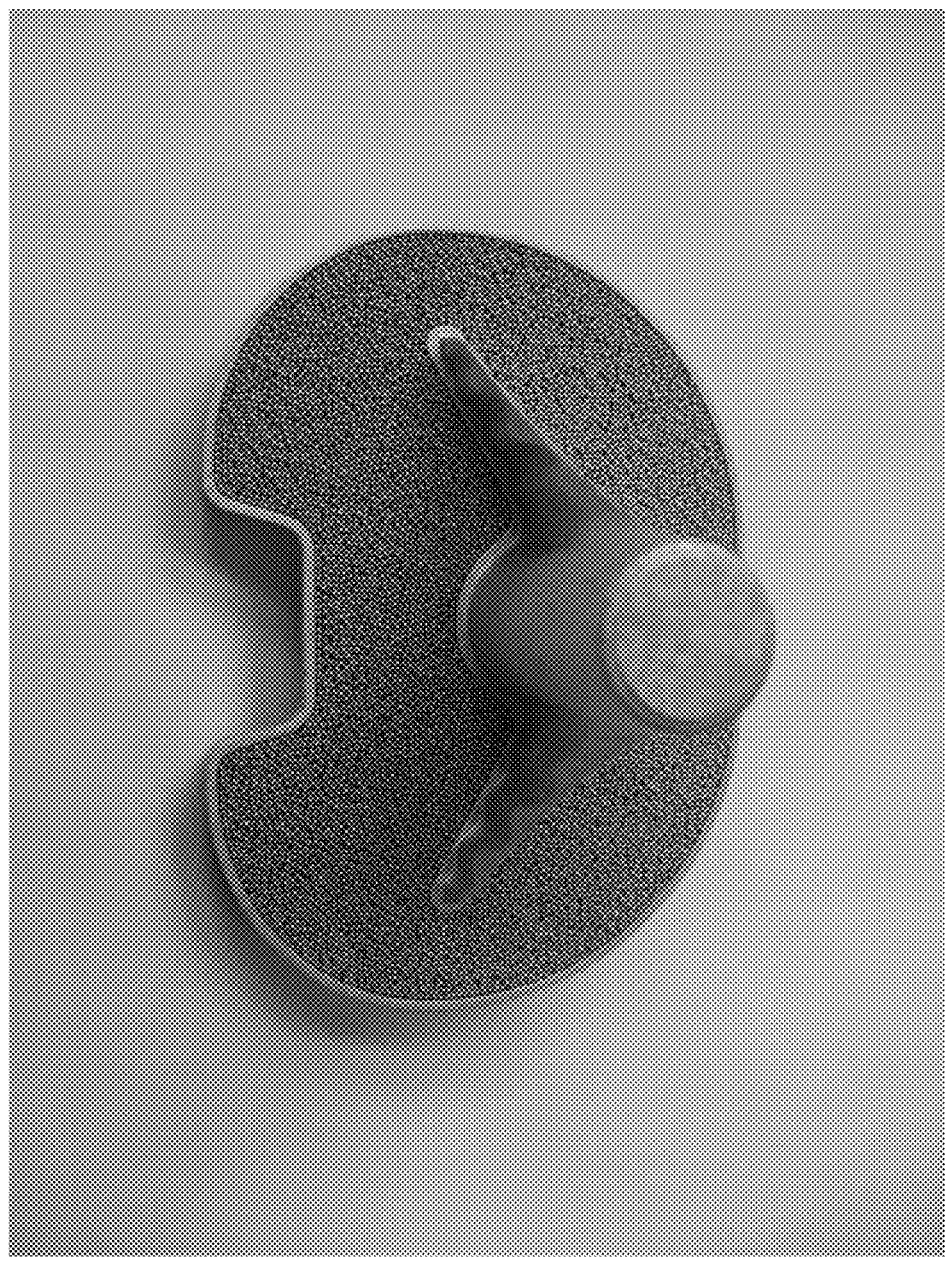
FIGS. 7 through 13 are photographs of surgical implant components.
Figure 8:
Figure 9:
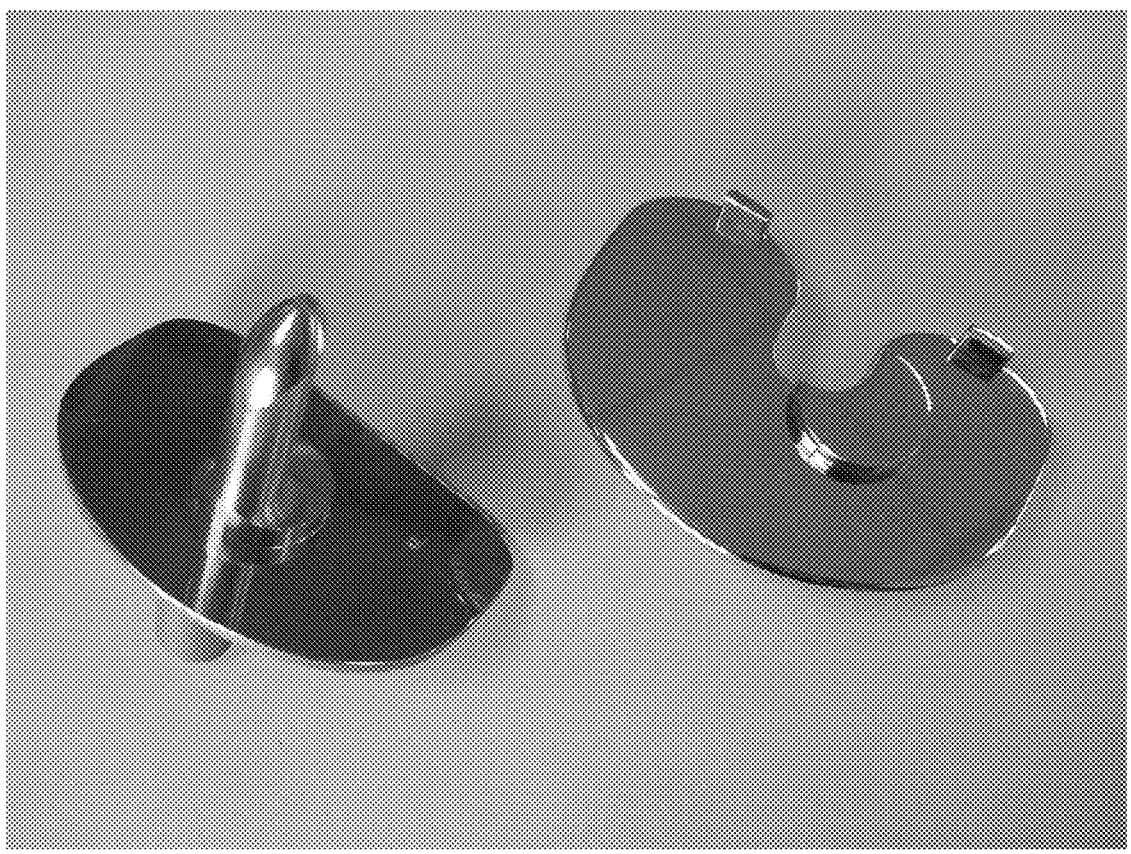
Figure 10:
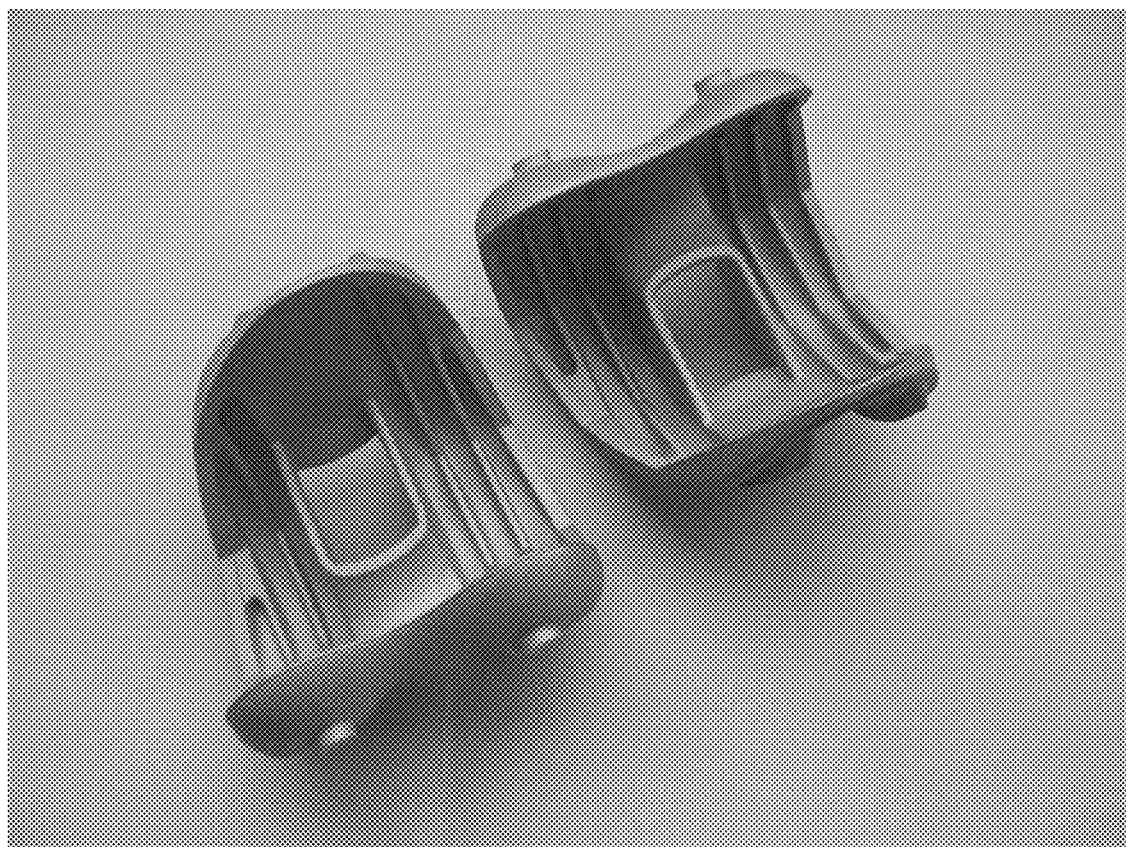
Figure 11:
Figure 12:
Figure 13:
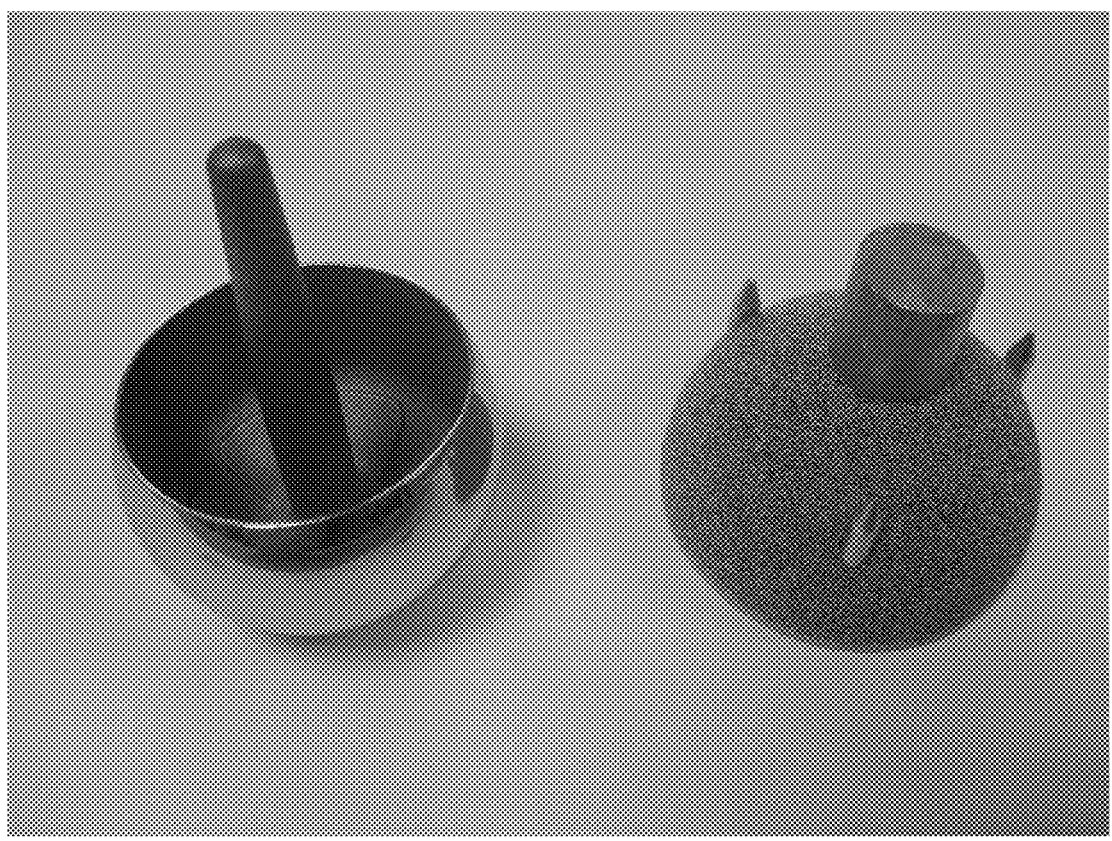

FIG. 7 is a photograph of a tibia plate implant component. FIG. 8 shows a knee implant component. FIG. 9 shows a tibia plate implant component. FIG. 10 shows a knee implant component. FIG. 11 shows a head implant component. FIGS. 12 and 13 show head cup implant components of hips.

Example VI

Figure 14:
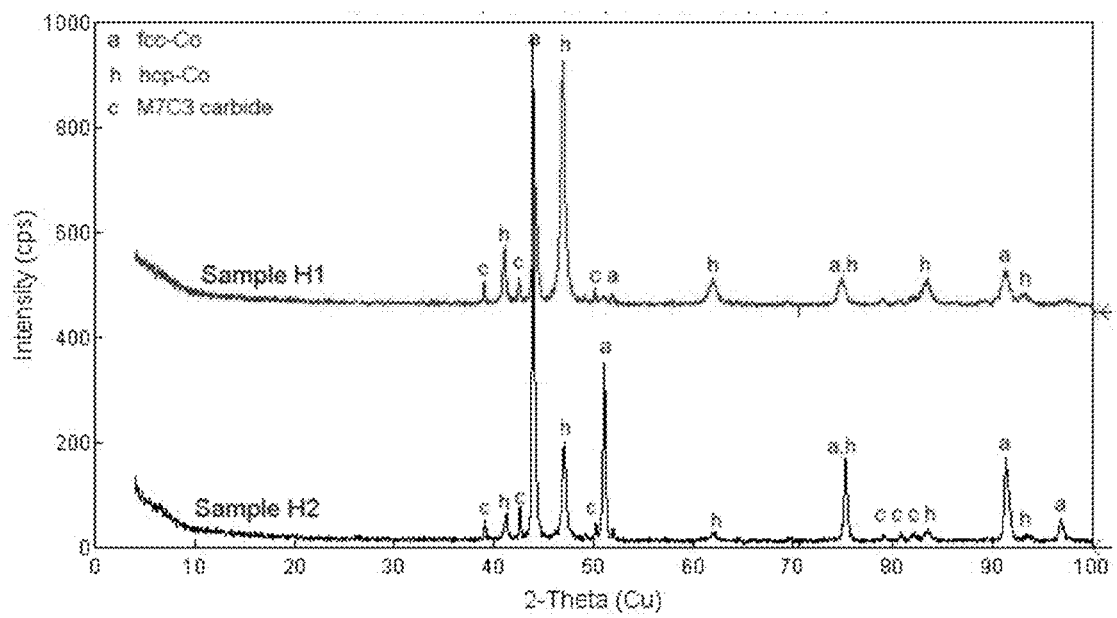
FIGS. 14 through 16 show X-ray diffraction patterns for alloys described in the examples.

The X-ray diffraction patterns of FIG. 14 were generated for the implant component alloys described above as 720 (Sample H1) and 712 (Sample H2). These pattern show the implant component alloy 720 is about 50 vol % each of FCC and HCP. The implant component alloy 712 is about 20 vol % of HCP and 80 vol % FCC.

Figure 15:
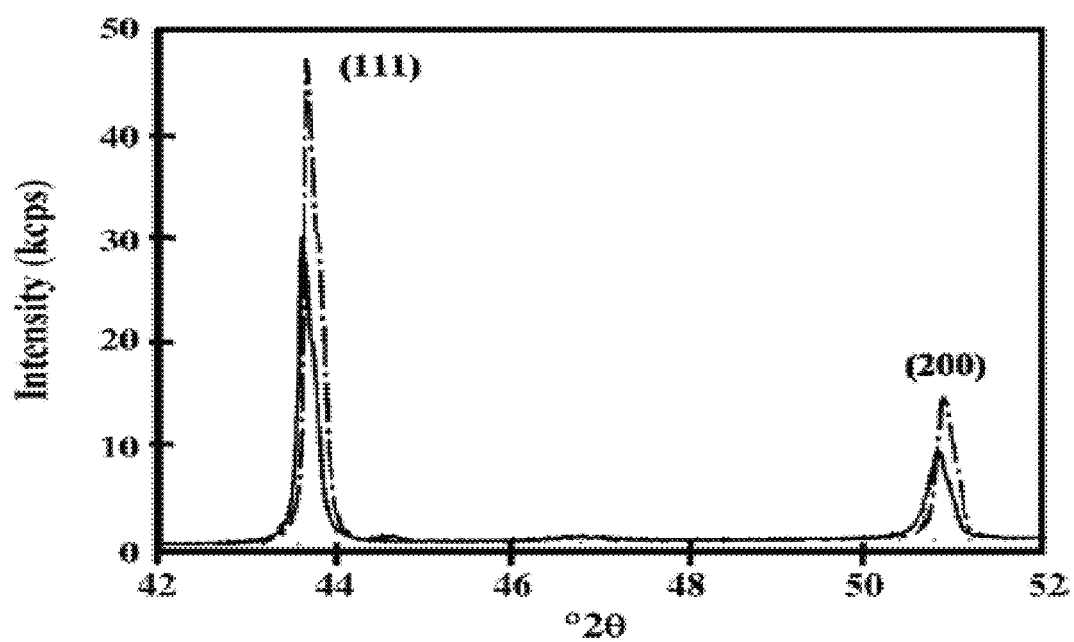
Figure 16:
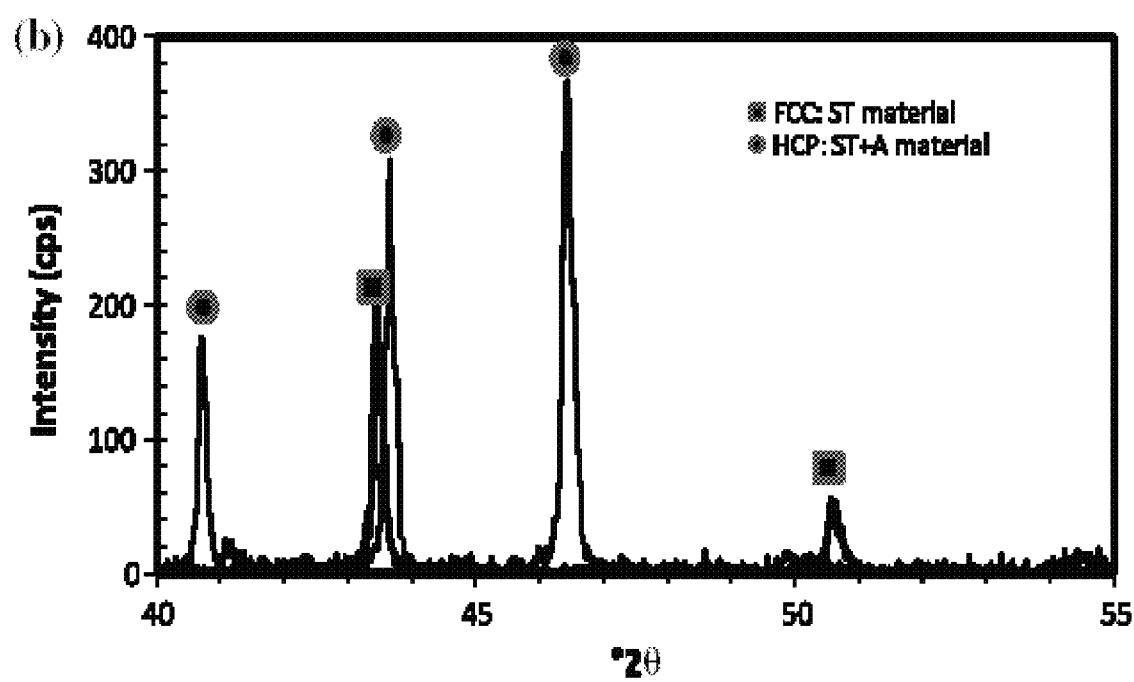

For comparison, FIG. 15 shows X-ray diffraction patterns of a lower C, lower Mo, Co-27Cr-5Mo-0.05C alloy with predominantly FCC before and after homogenization (aging). The unbroken line is the alloy as formed; the dashed line is after homogenization at 1150° C. for 30 minutes plus water quench. FIG. 16 shows X-ray diffraction patterns of as-received Co-27Cr-5Mo-0.23C obtained after a solution treatment (15 mins at 1150° C. followed by water quenching) which is predominately FCC; and the same alloy after isothermal aging (12 hours at 850° C.) in which a portion of HCP is formed.

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

In view of the above, it will be seen that several advantages of the invention are achieved and other advantageous results attained.

The above description illustrates the invention by way of example and not by way of limitation. This description clearly enables one skilled in the art to make and use the invention, and describes several embodiments, adaptations, variations, alternatives and uses of the invention, including what is presently believed to be the best mode of carrying out the invention. Additionally, it is to be understood that the invention is not limited in its application to the details of construction and the arrangement of components set forth in the following description or illustrated in the drawings. The invention is capable of other embodiments and of being practiced or carried out in various ways. Also, it will be understood that the phraseology and terminology used herein is for the purpose of description and should not be regarded as limiting.

The invention claimed is:

1. A surgical implant component comprising:
an implant component body manufactured from an alloy comprising:
from about 23 to about 33 wt % Cr,
from about 8 to about 20 wt % Mo,
from about 0.05 to about 1.5 wt % Si,
from about 0.35 to about 3.5 wt % C,
from about 40 to about 60 wt % Co, and
incidental impurities,
wherein the alloy has an atomic % ratio of (Cr+Mo+Nb)/Co of at least 0.59;
wherein the implant component body has a mixed face-centered cubic (FCC) and hexagonal close-packed (HCP) matrix metallurgical microstructure comprising between about 45% and about 85% by volume face-centered cubic structure, and between about 15% and about 55% by volume hexagonal close-packed structure; and
wherein the implant component body has a Rockwell C hardness of greater than 35; and
wherein the implant component is a component of an implant for repair or replacement of a component of a knee, hip, shoulder, elbow, wrist, ankle, finger, toe or spine.

2. The surgical implant component of claim 1 wherein the implant component is said knee, hip, or spine implant component.

3. The surgical component of claim 1 wherein the alloy comprises from about 1.5 to 3.5 wt % C.

4. The surgical component of claim 1 wherein any Ni and Fe present is strictly controlled to no more than 1 wt % each element.

5. The surgical component of claim 3 wherein any Ni and Fe present is strictly controlled to no more than 1 wt % each element.

6. The surgical component of claim 3 wherein any Ni and Fe present is strictly controlled to no more than 0.7 wt % each element.

7. The surgical implant component of claim 1 comprising:
the implant component body manufactured from the alloy and the alloy consists essentially of:
from about 23 to about 33 wt % Cr,
from about 8 to about 20 wt % Mo,
from about 0.05 to about 1.5 wt % Si,
from about 1.5 to about 3.5 wt % C,
from about 40 to about 60 wt % Co, and
incidental impurities totaling less than 4 wt % including no more than 1 wt % Fe and no more than 1 wt % Ni,
wherein the implant body has about 10 to about 35 wt % carbides in the matrix metallurgical microstructure comprising between the about 45% and about 85% by volume face-centered cubic structure, and the between about 15% and about 55% by volume hexagonal close-packed structure;
wherein the implant component body has a Rockwell C hardness of between 45 and 60.

8. The surgical implant component of claim 1 comprising:
the implant component body manufactured from the alloy and the alloy comprises:
from about 23 to about 33 wt % Cr,
from about 8 to about 20 wt % Mo,
from about 0.05 to about 1.5 wt % Si, from about 1.5 to about 3.5 wt % C,
from about 40 to about 60 wt % Co, and
incidental impurities totaling less than 4 wt % including no more than 1 wt % Fe and no more than 1 wt % Ni,
wherein the alloy has the atomic % ratio of (Cr+Mo+Nb)/Co of at least 0.59;
wherein the implant body has about 10 to about 35 wt % carbides in the matrix metallurgical microstructure comprising between the about 45% and about 85% by volume face-centered cubic structure, and the between about 15% and about 55% by volume hexagonal close-packed structure;
wherein the implant component body is one of the group consisting of forged, cast, or powder metallurgy manufactured;
wherein the implant component body is work hardened exclusively by cooling from its formation temperature and is cold-working-free; and
wherein the implant component body has a Rockwell C hardness of between 45 and 60.

9. The surgical implant component of claim 8 wherein the implant component body is active-work-hardening-free.

10. The surgical implant component of claim 8 wherein the alloy consists essentially of:
from about 23 to about 33 wt % Cr,
from about 8 to about 20 wt % Mo,
from about 0.05 to about 1.5 wt % Si,
from about 0.02 to about 1.5 wt % Mn,
from about 1.5 to about 3.5 wt % C,
from about 40 to about 60 wt % Co, and
incidental impurities totaling less than 4 wt % including no more than 1 wt % Fe and no more than 1 wt % Ni.

11. The surgical implant component of claim 1 wherein the implant component body has a Rockwell C hardness of greater than 45 up to 60.

12. The surgical implant component of claim 1 comprising between 0.2 and 0.8 wt % C and further comprising in the range of between 3 and 4.5 wt % Ni.

13. A method for manufacturing a surgical implant component body for a surgical implant comprising:
forming the surgical implant component body by a manufacturing method selected from the group consisting of casting, forging, and powder metallurgy pressing-plus-sintering from an alloy comprising:
from about 23 to about 33 wt % Cr,
from about 8 to about 20 wt % Mo,
from about 0.05 to about 1.5 wt % Si,
from about 0.35 to about 3.5 wt % C,
from about 40 to about 60 wt % Co, and
incidental impurities;
excluding any cold working by rolling, drawing, swaging, shot-peening or laser-peening;
wherein the alloy has an atomic % ratio of (Cr+Mo+Nb)/Co of at least 0.59;
wherein the implant body has a mixed face-centered cubic (FCC) and hexagonal close-packed (HCP) matrix metallurgical microstructure comprising between about 45% and about 85% by volume face-centered cubic structure, and between about 15% and about 55% by volume hexagonal close-packed structure;
wherein the implant component is a component of an implant for repair or replacement of a component of a knee, hip, shoulder, elbow, wrist, ankle, finger, toe or spine.

14. The method of claim 13 wherein the method further comprises work hardening exclusively by passive work hardening by cooling from an implant component formation temperature and excluding any active work hardening.

15. The method of claim 13 wherein the alloy comprises from about 1.5 to 3.5 wt % C.

16. A surgical implant component formed by the method of claim 13, the component comprising:
the implant component body manufactured from the alloy comprising:
from about 23 to about 33 wt % Cr,
from about 8 to about 20 wt % Mo,
from about 0.05 to about 1.5 wt % Si,
from about 0.35 to about 3.5 wt % C,
from about 40 to about 60 wt % Co, and
incidental impurities,
wherein the alloy has the atomic % ratio of (Cr+Mo+Nb)/Co of at least 0.59;
wherein the implant component body has the matrix metallurgical microstructure comprising between about 45% and about 85% by volume face-centered cubic structure, and between about 15% and about 55% by volume hexagonal close-packed structure; and
wherein the implant component body has a Rockwell C hardness of greater than 35.

17. The surgical implant component of claim 16 wherein the implant component is a component of an implant for repair or replacement of a component of a knee, hip, shoulder, finger, elbow, wrist, ankle, finger or spine.

18. The surgical implant component of claim 16 wherein the implant body has about 10 to about 35 wt % carbides in the matrix metallurgical microstructure comprising between the about 45% and about 85% by volume face-centered cubic structure, and the between about 15% and about 55% by volume hexagonal close-packed structure.

19. The surgical implant component of claim 1 wherein the alloy consists of:
from about 23 to about 33 wt % Cr,
from about 8 to about 20 wt % Mo,
from about 0.05 to about 1.5 wt % Si,
from about 0.35 to about 3.5 wt % C,
from about 0.02 to about 1.5 wt % Mn,
from about 40 to about 60 wt % Co, and
incidental impurities.

20. The surgical implant component of claim 1 wherein the alloy consists of:
from about 23 to about 33 wt % Cr,
from about 8 to about 20 wt % Mo,
from about 0.05 to about 1.5 wt % Si,
from about 1.5 to about 3.5 wt % C,
from about 0.02 to about 1.5 wt % Mn,
from about 40 to about 60 wt % Co, and
incidental impurities totaling less than 4 wt % including no more than 1 wt % Fe and no more than 1 wt % Ni.

21. The surgical implant component of claim 1 wherein the alloy comprises Mn in a range from about 0.05 to about 1.5 wt %.

22. The surgical implant component of claim 1 wherein the alloy comprises Mn in a range from about 0.2 to about 1 wt %.

* * * * *